United States Patent [19]

Demaline

[11] Plant 4,815

[45] Jan. 26, 1982

[54] WHITE FLOWERING CRABAPPLE TREE

[75] Inventor: Lester L. Demaline, Avon, Ohio

[73] Assignee: Willoway Nurseries, Inc., Avon, Ohio

[21] Appl. No.: 130,144

[22] Filed: Mar. 13, 1980

[51] Int. Cl.[3] ..... A01H 5/00

[52] U.S. Cl. ..... Plt./34

[58] Field of Search ..... Plt./34

*Primary Examiner*—James R. Feyrer

*Attorney, Agent, or Firm*—Maky, Renner, Otto & Boiselle

[57] ABSTRACT

A flowering crabapple tree is disclosed herein having a straight, cherry colored trunk and upright secondary branching to form a tree having a pyramidal shape; profuse, white flowers over the entire tree in blooming season, and glossy, wine-red fruit providing a color contrast to the emerald green leaves which change to a light yellow color before dropping.

5 Drawing Figures

1

The present invention or discovery relates to a new and distinct variety of Malus, a flowering crabapple tree, originated by me and having unusual and distinctive growth patterns, structural form and appearance.

In particular, my new flowering crabapple tree exhibits a very vigorous growth pattern in its first two to three years. After reaching the third year, its growth rate slows somewhat, which is a desirable characteristic. This tree holds its green leaves until very late in the fall season and even retains such green color for a brief period after the onset of freezing weather. The green fall leaf color then changes to a light yellow leaf color that contrasts with the dark wine-red fruit held by this tree until mid-winter. An outstanding feature of my tree is the upright pyramidal form which is unusual for a white flowering crabapple tree.

The principal novel and distinctive characteristics of this new variety are considered to be, in combination (1) The overall structural form including a very straight trunk with upright secondary branching and distinctively pyramidal form.

(2) The cherry colored bark that is spined with a light color protrusion resembling cherry bark.

(3) The leaf structure which is medium in size and a dark emerald green in color with no evidence to date of any crabapple diseases.

(4) The dark, wine-red fruit which is of desirable size and remains on the tree until mid-winter.

(5) The medium size white flower bloom in five and sometimes four-petaled clusters covering the entire tree during its blooming period.

My new flowering crabapple tree has been propagated asexually at Avon, Ohio by budding and by grafting, and the tree can be readily propagated in this manner perpetuating all of its original characteristics. In fact, this crabapple tree has a unique feature in that it roots very well from soft-wood cuttings.

The original parent specimen was discovered and selected by me as a seedling from a number of seedlings at my nursery. This crabapple tree has proved to be hardy in Avon, Ohio, which is in Zone 5. In addition, my crabapple tree was propagated from buds in 1977 and 1978 in an experimental test program and in 1979 in a program to begin development of commercial inventory in Gresham, Oreg., which is in Zone 7.

Referring now more particularly to the drawing;

2

FIG. 3 shows such crabapple tree in its upright, pyramidal form with distinctive upright branching;

The following is a specific description of such new flowering crabapple tree based on the ISCC-NBS Centroid Color Code.

The original tree is approximately 12 ft. tall and exhibits a pyramidal growth habit with upright branching. Because of its pyramidal growth habit, this crabapple tree will do very well in general landscaping and should do especially well in confined growing areas, such as street tree plantings or condominium court yards.

Figure 1:
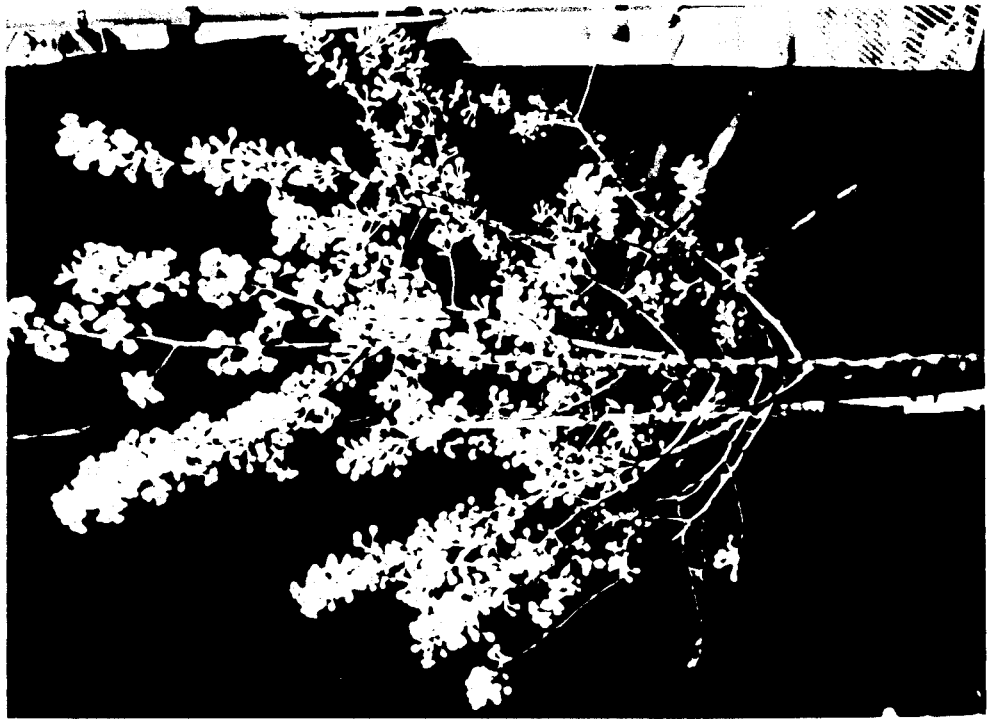
FIG. 1 shows my new flowering crabapple tree in full bloom with its natural pyramidal form.
Figure 5:
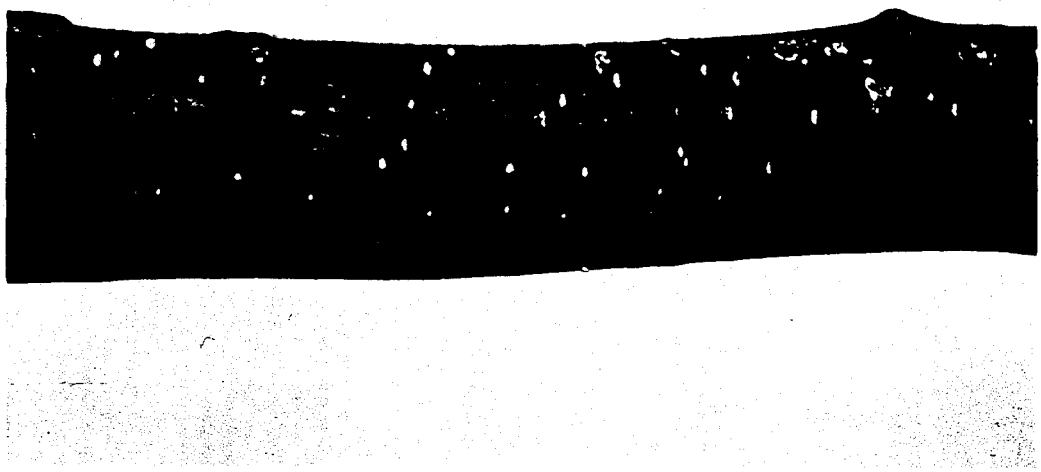
FIG. 5 shows a section of the trunk of my crabapple tree having the very dark cherry bark with lightly colored spines resembling protrusions of cherry bark.

As thus shown in FIGS. 1 and 3, the trunk is very straight and free of cross-branching. The trunk, main lower stem and secondary branching have cherry bark (55 S. Br.) in the first growth year which changes to a very dark cherry bark (65 br. Black) in the second growth year. As best shown in FIG. 5, the very dark cherry bark has lightly colored, reddish brown spines (45 l. gy. r. Br.) resembling protrusions of cherry bark. In approximately the fourth or fifth growth year with further wood maturation, the bark on the trunk and main lower stem has returned to a cherry coloration (55 S. Br.) with lightly colored spines (45 l. gy. r. Br.) resembling cherry bark. With such further maturation, the upper stem structure is of brownish-gray color (61 gy. Br.), and the side buds of the primary branching are 3–5 mm. and are brown to slightly gray (64 br. Gray) in color.

Figure 2:
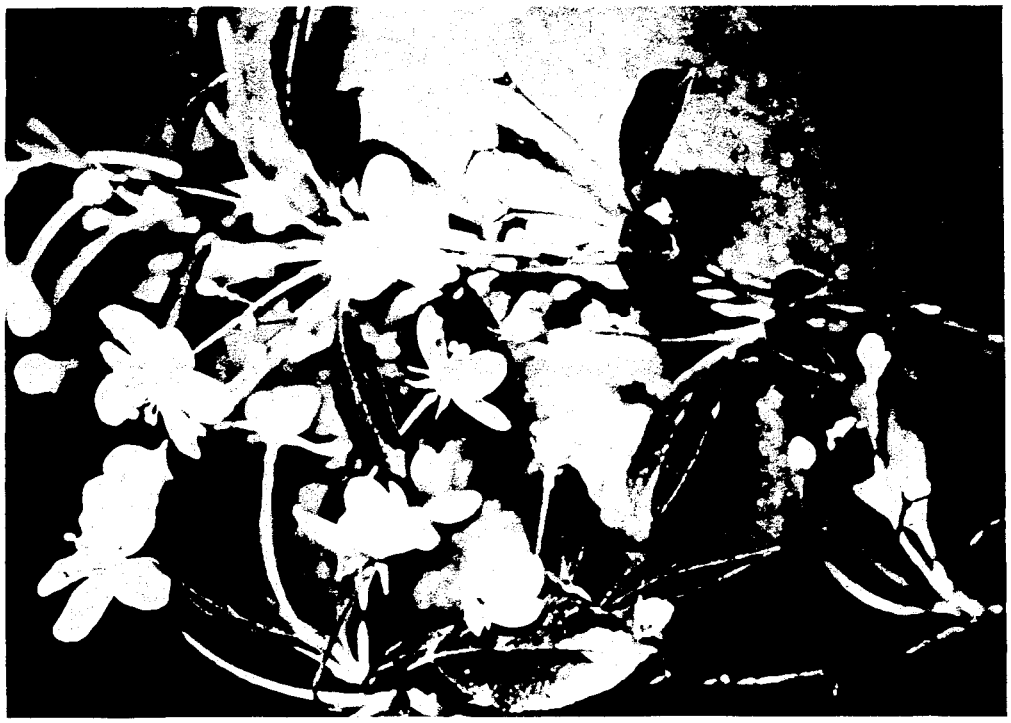
FIG. 2 shows the leaves, flowers and buds of such crabapple tree.

The leaves, which are 7.0 to 8.0 cm. long and 3.0 to 4 cm. wide, are very strong and leathery to the touch and are deep emerald green (126 d. Ol. G.) in color. As best shown in FIG. 2, the leaves are slightly upwardly cupped and have a saw-tooth peripheral edge with each V-shaped depression being approximately 1.0 mm. deep and 2.0 mm. across at the peripheral edge. The leaves retain their green color until late in the fall season as demonstrated by the leaves still being green on Nov. 20, 1979. The leaves may even briefly retain their green color after experiencing freezing weather, but then change to a light yellow color (84 s. Y.) for a several week period before dropping.

In blooming season, the flowers are borne in clusters of 5 to 8 per cluster and are very profuse along the branches, covering the entire tree as shown in FIG. 1. They are displayed prominently on stiff, long pedicels, 3.0–4.0 cm. long. As shown in FIG. 2, the immature bud is a reddish-pink (12 s. Red) changing to a creamy green color (121 p. YG.) as the bud matures. The open flowers, which are 2.0–3.0 cm. across, are single and essentially white (263 White) as the flower opens changing to pure white (92 y. White) with age. There are usually 5 and sometimes 4 petals which are 1.0–1.6 cm. long per bloom, with the blooms being well-rounded on their outer ends. The peak flowering time for my crabapple tree is May 5 to May 14.

Figure 4:
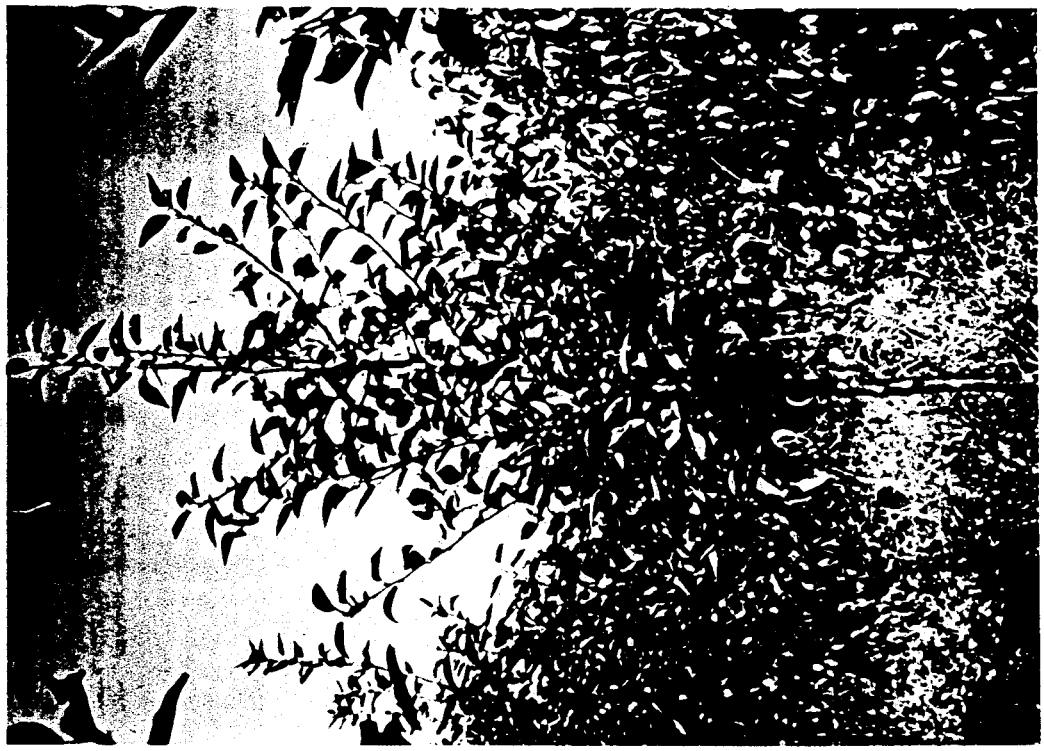
FIG. 4 shows the fall fruit of such tree which is very abundant and of a very desirable wine-red color.
Figure 4:
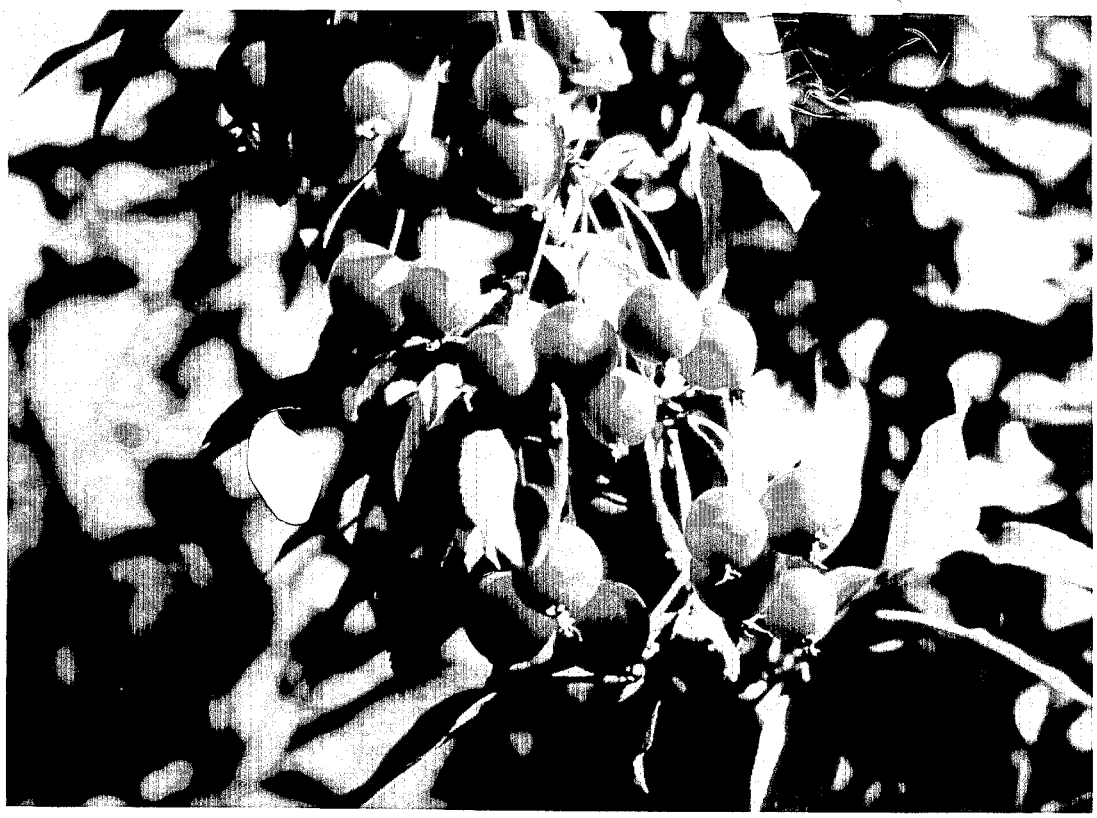

The fruit is small, approximately 1.2 cm. in diameter, and is mostly round in shape. As best shown in FIG. 4, the fruit is borne in clusters of 3 to 5 on a stem of 3.0–4.0 cm. in length, with such fruit being well distributed on the entire tree at maturity. The color of the glossy fruit at maturity is wine-red (13 d. Red). The calyx end is quite prominent as it has a prominent cup and the stem end has the same cupping effect. The fruit is very firm and holds on the tree until mid-December, contrasting well with the leaf coloration both before and after color change. If not eaten by birds, the remaining fruit has been known to hold on the tree until spring as is shown by the fruit remaining on the flowering tree pictured in FIG. 1. The fruit as it becomes overly ripe changes in color to a combination of red and brown (13 d. Red and 40 S. r. Br.).

I claim:

1. A new and distinct variety of flowering crabapple tree, *Malus cultivar,* substantially as shown and described herein.

* * * * *